United States Patent [19]

Foxton et al.

[11] Patent Number: 4,985,407
[45] Date of Patent: Jan. 15, 1991

[54] DIPEPTIDE COMPOUNDS, PROCESSES FOR THEIR PREPARATION AND COMPOSITIONS CONTAINING THEM

[75] Inventors: Michael W. Foxton, Chalfont St. Giles; Barry E. Ayres, Ickenham; Anthony W. J. Cooper, Northolt, all of England

[73] Assignee: Glaxo Group Limited, England

[21] Appl. No.: 280,330

[22] Filed: Dec. 6, 1988

[30] Foreign Application Priority Data

Dec. 7, 1987 [GB] United Kingdom ................ 8728561

[51] Int. Cl.$^5$ ............................................. C07K 5/06
[52] U.S. Cl. ..................... 514/19; 530/331; 546/210; 548/336; 548/344
[58] Field of Search .................. 514/19; 546/210; 548/336, 344; 530/331

[56] References Cited

U.S. PATENT DOCUMENTS

| | | | |
|---|---|---|---|
| 4,533,656 | 8/1985 | Walker | 514/19 |
| 4,548,926 | 10/1985 | Matsueda et al. | 514/19 |
| 4,616,088 | 10/1986 | Ryono et al. | 548/344 |
| 4,665,193 | 5/1987 | Ryono et al. | 546/278 |
| 4,719,288 | 1/1988 | Fuhrer et al. | 548/455 |
| 4,746,649 | 5/1988 | Raddatz et al. | 514/19 |

FOREIGN PATENT DOCUMENTS

| | | |
|---|---|---|
| 0163237 | 12/1985 | European Pat. Off. |
| 0173481 | 3/1986 | European Pat. Off. |
| 0184550 | 6/1986 | European Pat. Off. |
| 0212903 | 3/1987 | European Pat. Off. |
| 084/03044 | 8/1984 | World Int. Prop. O. |
| 87/02581 | 5/1987 | World Int. Prop. O. |
| 87/05302 | 9/1987 | World Int. Prop. O. |

Primary Examiner—Lester L. Lee

Attorney, Agent, or Firm—Bacon & Thomas

[57] ABSTRACT

There are described new compounds of formula (1)

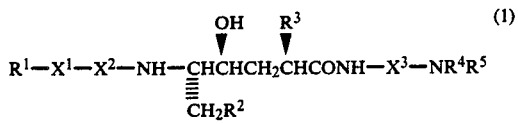

wherein
  $R^1$ represents an acyl group;
  $X^1$ represents phenylalanine or p-methoxyphenylalanine bonded N-terminally to $R^1$ and C-terminally to $X^2$;
  $X^2$ represents histidine or N-methylhistidine bonded N-terminally to $X^1$ and C-terminally to the group —NH—;
  $R^2$ represents a $C_{4-6}$ cycloalkyl group;
  $R^3$ represents a group $CHR^6R^7$ is a hydrogen atom and $R^7$ is a phenyl group, or $R^6$ is a methyl group and $R^7$ is a hydrogen atom or a methyl or ethyl group;
  $X^3$ represents a $C_{2-6}$ alkylene chain optionally substituted by one or more $C_{1-4}$ alkyl groups;
  $R^4$ and $R^5$, which may be the same or different, each independently represent a hydrogen atom or a $C_{1-4}$ alkyl group, or $NR^4R^5$ may form a 5- or 6- membered polymethylenimine ring;
  and salts and solvates thereof.

The new compounds have been found to exhibit activity as renin inhibitors, combining good duration of action with significant oral potency.

Compositions containing the compounds of formula (1) and processes for preparing the compounds are also described.

20 Claims, No Drawings

DIPEPTIDE COMPOUNDS, PROCESSES FOR THEIR PREPARATION AND COMPOSITIONS CONTAINING THEM

This invention relates to a series of dipeptides which inhibit renin, to processes for their preparation, to pharmaceutical compositions containing them and to their use in medicine.

WO 84/03044, EP-A-0163237, EP-A-0173481, EP-A-0184550 and EP-A-0212903 disclose compounds which are stated as useful as renin inhibitors. We have now found that a small group of dipeptides generically embraced by the disclosures in the aforementioned patent specifications, but not specifically disclosed therein, are highly active renin inhibitors having advantageous properties. In particular, the compounds of the present invention are highly selective inhibitors of the action of the natural enzyme renin. They also have a particularly advantageous combination of good duration of action with significant oral potency. Furthermore, the dipeptides of the present invention exhibit advantageous physico-chemical properties.

Thus, according to one aspect of the present invention, we provide the compounds of formula (1)

$$R^1-X^1-X^2-NH-\underset{\underset{CH_2R^2}{|}}{C}H-CHCH_2CH(OH)-CONH-X^3-NR^4R^5 \quad (1)$$

(with $R^3$ and OH substituents as shown)

wherein
- $R^1$ represents an acyl group;
- $X^1$ represents phenylalanine or p-methoxyphenylalanine bonded N-terminally to $R^1$ and C-terminally to $X^2$;
- $X^2$ represents histidine or N-methylhistidine bonded N-terminally to $X^1$ and C-terminally to the group —NH—;
- $R^2$ represents a $C_{4-6}$ cycloalkyl group;
- $R^3$ represents a group $CHR^6R^7$ (where $R^6$ is a hydrogen atom and $R^7$ is a phenyl group, or $R^6$ is a methyl group and $R^7$ is a hydrogen atom or a methyl or ethyl group;
- $X^3$ represents a $C_{2-6}$ alkylene chain optionally substituted by one or more $C_{1-4}$ alkyl groups;
- $R^4$ and $R^5$, which may be the same or different, each independently represent a hydrogen atom or a $C_{1-4}$ alkyl group, or $NR^4R^5$ may form a 5 or 6 membered polymethylenimine ring;

and salts and solvates (eg hydrates) thereof.

It will be appreciated that, for pharmaceutical use, the salts referred to above will be the physiologically acceptable salts, but other salts may find use, for example in the preparation of the compounds of formula (1) and the physiologically acceptable salts thereof.

Suitable salts of the compounds of formula (1) include acid addition salts formed with organic or inorganic acids (for example hydrochlorides, hydrobromides, sulphates, phosphates, nitrates, benzoates, naphthoates, hydroxynaphthoates, p-toluenesulphonates, methanesulphonates, sulphamates, ascorbates, oxalates, tartrates, salicylates, succinates, lactates, glutarates, gluconates, acetates, trifluoroacetates, tricarballylates, citrates, fumarates and maleates).

It will also be appreciated that the compounds of formula (1) may contain one or more undefined chiral centres and the invention includes all individual optical isomers of the compounds of formula (1) as well as mixtures thereof. However, it is to be understood that the $R^3$, OH and $CH_2R^2$ groupings always retain the relative configurations shown in formula (1). It is to be further understood that the amino acid residues $X^1$ and $X^2$ always have the natural L-configuration.

References hereinafter to compounds of formula (1) and their use and preparation should, unless the context dictates otherwise, be taken to be references to the compounds and their salts, eg the physiologically acceptable salts.

In the compounds of formula (1), the 'acyl group' within the definition of $R^1$ may be, for example, a group $R^8X^4C(=O)$— where $R^8$ is a $C_{1-6}$ alkyl group and $X^4$ is an oxygen atom or a bond.

The term 'N-methylhistidine' within the definition of $X^2$ means a histidine group containing a methyl substituent attached to the amide nitrogen atom linking $X^1$ and $X^2$.

The term 'alkyl' as defined within $X^3$, $R^4$, $R^5$ and $R^8$ may be a straight or branched chain alkyl group. Examples of suitable alkyl groups include methyl, ethyl, n-propyl, i-propyl, n-butyl, s-butyl and t-butyl.

When $R^4$ or $R^5$ are alkyl groups or $X^3$ contains an alkyl substituent this is preferably methyl.

$R^1$ preferably represents a group $R^8X^4C(=O)$— where $R^8$ is a $C_{1-4}$ alkyl group and $X^4$ is an oxygen atom or a bond. Examples of such groups include acetyl, ethoxycarbonyl and t-butyloxycarbonyl.

$R^2$ preferably represents a cyclopentyl group or, more preferably, a cyclohexyl group.

$X^3$ preferably represents a $C_{2-4}$ alkylene chain optionally substituted by one or two methyl groups. Examples of such chains include —$(CH_2)_2$—, —$CH_2C(CH_3)_2$— and —$(CH_2)_4$—.

Preferably $R^4$ and $R^5$ each independently represent a hydrogen atom or a methyl group, more preferably each represent a hydrogen atom.

A preferred class of compounds of the invention are those represented by formula (1a)

$$R^1-X^1-X^2-NH-\underset{\underset{CH_2-cyclohexyl}{|}}{C}H-CHCH_2CH(OH)-CONH-X^3-NR^4R^5 \quad (1a)$$

wherein $R^1$ represents a group $R^8X^4C(=O)$— where $R^8$ is a $C_{1-4}$ alkyl group and $X^4$ is an oxygen atom or a bond; $X^1$, $X^2$ and $R^3$ are as defined in formula (1) above; $X^3$ represents a $C_{2-4}$ alkylene chain optionally substituted by one or two methyl groups; and $R^4$ and $R^5$ each represent a hydrogen atom or a methyl group.

A preferred group of compounds from within this preferred class are those in which $R^1$ represents an acetyl or t-butoxycarbonyl group, $X^1$ represents phenylalanine, $X^2$ represents histidine, $R^3$ represents a group $CHR^6R^7$ where $R^6$ represents a hydrogen atom and $R^7$ represents a methyl or preferably a phenyl group, $X^3$ represents a chain —$(CH_2)_4$—, —$CH_2CH(CH_3)$— or, more preferably, —$(CH_2)_2$— and $R^4$ and $R^5$ each independently represent a hydrogen atom or a methyl group, more particularly each represent a hydrogen atom.

A preferred compound according to the invention is N-[(1,1-dimethylethoxy)carbonyl]-L-phenylalanyl-N-[1S-(cyclohexylmethyl)-2S-hydroxy-5-[[2-aminoethyl]amino]-5-oxo-4R-(phenylmethyl)pentyl]-L-histidinamide and its salts, especially physiologically acceptable salts, and solvates.

Compounds of formula (1) have been shown both in vitro and in vivo to inhibit the action of the natural enzyme renin.

Human renin inhibitory potency was determined in vitro by measuring the ability of the test compound to inhibit endogenous plasma renin generation of angiotensin I from endogenous substrate at pH 7.4. Liberated angiotensin I was measured by an antibody-trapping radioimmunoassay technique based on methods described by K. Poulsen and J. Jorgensen in J. Clin. Endocrinol. Metab. (1974), 39, 816–825 and M. Szelke et al. in Hypertension (1987), 4, Suppl. II, 59–69.

Inhibition of plasma renin activity was also assessed in the conscious chronically-cannulated normotensive marmoset according to the method of C. J. Gardner and D. J. Twissell in Brit. J. Pharmacol. (1985) 86, 620P. Frusemide (5 mg/kg i.v.) was administered to the marmoset 30 minutes before the beginning of the experiment in order to elevated and stabilize renin levels. The plasma renin activity was measured according to the aforementioned procedure.

Compounds according to the invention may therefore be of particular use in the treatment of hypertension. They are also potentially useful for the treatment of other diseases such as hyperaldosteronism, cardiac insufficiency, congestive heart failure, post-myocardial infarction, cerebrovascular disorders, glaucoma and disorders of intracellular homeostasis.

Compounds according to the invention also have favorable physico-chemical properties. Thus, for example, compounds of the invention have good water solubility at near to physiological pH [e.g. pH 6.0 to 8.0] which makes them particularly suitable for parenteral administration.

According to a further aspect of the invention we provide a compound of formula (1) or a physiologically acceptable salt thereof for use in the treatment of the aforementioned diseases, especially hypertension.

According to another aspect of the invention we provide the use of a compound of formula (1) or a physiologically acceptable salt thereof for the manufacture of a therapeutic agent for the treatment of the aforementioned diseases, especially hypertension.

According to a further aspect of the invention we provide a method of treating the aforementioned diseases, especially hypertension, which method comprises administering an effective amount of a compound of formula (1) or a physiologically acceptable salt thereof to the patient.

It will be appreciated that the compounds of formula (1) may advantageously be used in conjunction with one or more other therapeutic agents, such as for example diuretics and/or different antihypertensive agents. It is to be understood that the present invention covers the use of a compound of formula (1) or a physiologically acceptable salt thereof in combination with one or more other therapeutic agents.

The compounds of the invention may be formulated in any convenient manner with one or more pharmaceutical carriers. Thus, a further aspect of the invention includes pharmaceutical compositions comprising a compound of formula (1) or a physiologically acceptable salt thereof formulated for oral, buccal, transdermal, parenteral or rectal administration or in a form suitable for administration by inhalation or insufflation. Oral administration is preferred.

For oral administration the pharmaceutical composition may take the form of for example tablets, which may be film or sugar coated, capsules, powders, granules, solutions including syrups, or suspensions prepared by conventional means with acceptable excipients.

For parenteral administration the compounds of formula (1) may be given as a bolus injection or by continuous infusion. The compositions may take such forms as suspensions, solutions or emulsions in oily or aqueous vehicles and may contain formulator agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of formula (1) may be formulated as ointments and creams for transdermal administration and as suppositories or retention enemas for rectal administration.

For buccal administration the composition may take the form of tablets or lozenges formulated in conventional manner.

For administration by inhalation the compounds according to the invention are conveniently delivered in the form of an aerosol spray presentation from pressurised packs with the use of a suitable propellant, e.g. dichlorodifluoromethane, trichlorofluormethane, dichlorotetrafluorethane, carbon dioxide or other suitable gas, or from a nebuliser. In the case of a pressurised aerosol the dosage unit may be determined by providing a valve to deliver a metered amount.

Alternatively, for administration by inhalation the compounds according to the invention may take the form of a dry powder composition, for example a powder mix of the compound and a suitable powder base such as lactose or starch. The power composition may be presented in unit dosage form in, for example, capsules or cartridges of e.g. gelation, or blister packs from which the powder may be administered with the aid of an inhaler or insufflator.

When the compositions comprise dosage units, each unit will preferably contain 5 mg to 500 mg, advantageously where the compounds are to be administered orally 25 mg to 400 mg of the active compound. The daily dosage as employed for adult human treatment will preferably range from 5 mg to 3 g, most preferably from 25 mg to 1 which may be administered in 1 to 4 daily doses, for example, depending on the route of administration and on the condition of the patient.

The compounds of formula (1) may be prepared by the following processes, wherein the various groups and symbols are as defined for formula (1) unless otherwise specified.

Thus, according to a further aspect of the present invention we provide a process for preparing the compounds of formula (1) which comprises treating the lactone of formula (2)

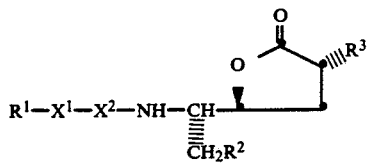 (2)

with a diamine of formula (3)

$$R^5R^4N-X^3-NH_2 \quad (3)$$

and, if desired, followed by salt formation.

The reaction may be effected in the absence or presence of a solvent at any suitable temperature eg room temperature to 80° C. Suitable solvents include alcohols or halogenated hydrocarbons (eg dichloromethane).

It will be appreciated that when $R^4$ and $R^5$ both represent hydrogen atoms it may be desirable to protect one of the two primary amino groups in the diamine (3) in order to effect the desired reaction. Suitable protecting groups include benzyloxycarbonyl or the primary amine may form a phthalimido group which may be removed using standard procedures.

Intermediates of formula (3) are either known compounds or may be prepared by methods analogous to those described for preparing the known compounds of formula (3).

The lactones of formula (2) may be prepared from compounds of formula (4)

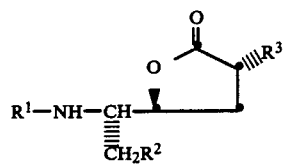 (4)

using well-known methods for introducing the amino acid residues $X^1$ and $X^2$.

Thus, for example, the compound (4) may be selectively hydrolysed e.g. with hydrogen chloride in dioxan or tetrahydrofuran or with trifluoroacetic acid to provide the compound (5)

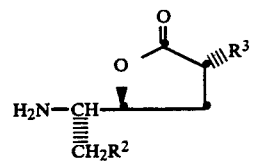 (5)

or a salt thereof (e.g. the hydrochloride salt).

The compound (5) or a salt thereof may then be treated with a carboxylic acid of formula (6)

$$R^1-X^1-X^2-OH \quad (6)$$

under dehydrating conditions to provide the desired intermediate of formula (2). The dehydration reaction may be effected in a suitable solvent (eg an amide such as dimethylformamide) in the presence of a dehydrating agent such as diphenylphosphoryl azide and preferably in the presence of a base such as triethylamine.

Alternatively, the compound (5) may be converted to the compound of formula (2) in a stepwise manner involving sequential reaction with the compounds of formulae (7) and (8)

$$R^1-X^2-OH \quad (7)$$

$$R^1-X^1-OH \quad (8)$$

or a suitable ester thereof, e.g. the pentafluorophenyl ester.

Reaction with the compounds (7) and (8) may be effected under dehydrating conditions analogous to those described just above. Reaction with e.g. the pentafluorophenyl esters of the compounds (7) and (8) may be similarly effected but using an amine such as 4-(2-aminoethyl)morpholine in place of the dehydrating agent.

It will be appreciated that the $R^1$ group will need to be removed after reaction with (7) and before reaction with (8). The $R^1$ group may be removed under acidic conditions as described previously.

It may be necessary to protect other active groups in the molecule when preparing a compound of formula (2). Thus, for example, when the compound of formula (2) is prepared in a stepwise manner from a compound of formula (5) the histidine imidazole NH group may need to be protected. Suitable protecting groups include 2,4-dinitrophenyl which may subsequently be removed under the general process conditions described above for preparing compounds of formula (1) from compounds of formulae (2) and (3).

The compounds of formulae (6), (7) and (8) are either known compounds or may be prepared from known compounds using standard methodology.

The compounds of formula (4) may be prepared from compounds of formula (9)

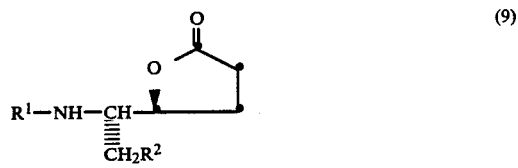 (9)

using methods for introducing the group $R^3$.

The conversion may be effected by reacting the compound (9) with a strong base e.g. sodium bistrimethylsilylamide or lithium diisopropylamide in a suitable solvent such as an ether (eg tetrahydrofuran) at a low temperature (eg $-70°$ C.) followed by treatment with a compound $R^3L$ where L is a leaving group such as halogen (eg bromine), alkanesulphonyloxy (eg methanesulphenyloxy or trifluoromethanesulphenyloxy) or arylsulphonyloxy (eg benzenesulfphonyloxy or p-toluenesulphonxyloxy).

The compounds of formula (9) are either known compounds described in EP-A-0212903 or may be prepared according to the methods described therein for preparing the known compounds of formula (9).

Alternatively, the compounds of formula (4) may be prepared from compounds of formula (10)

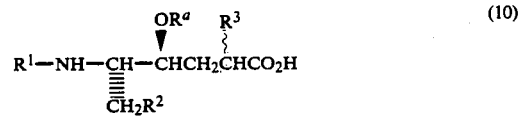 (10)

(where $R^a$ is a hydroxyl protecting group, eg acetyl) by treatment with an aqueous base (eg sodium hydroxide in aqueous ethanol) followed by N,N¹-dicyclohexylcarbodiimide in an alcoholic solvent such as ethanol or in a ester solvent such as ethyl acetate.

The compounds of formula (10) may be prepared from compounds of formula (11)

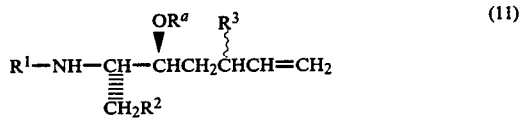

(where $R^a$ is as defined above) by peroxidation. The reaction may, for example, be effected using a periodate such as sodium metaperiodate in the presence of a suitable transition metal catalyst such as ruthenium trichloride. Conveniently, the compounds of formula (4) are prepared from compounds of formula (11) without isolating the intermediate compounds of formula (10).

The compounds of formula (11) may be prepared from compounds of formula (12)

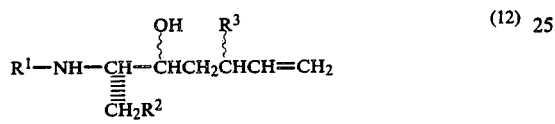

using standard procedures. Thus, for example, an acetyl group may be introduced by treating a compound (12) with acetic anhydride under basic conditions (e.g. using pyridine or 4-dimethylaminopyridine or a mixture thereof).

The compounds of formula (12) may be prepared from the known compounds of formula (13)

by a Grignard reaction with a known compound of formula (14)

(where Hal is a halogen atom, eg bromine) in a suitable solvent such as an ether (eg diethyl ether), and conveniently at room temperature.

When $R^1$ is a particular acyl protecting group this may be converted to a different acyl protecting group at any suitable stage in the overall synthesis of the compounds of the invention. Thus, for example, a t-butoxycarbonyl group may be converted to an acetyl group by first removing the t-butoxycarbonyl group by hydrolysis e.g. with hydrogen chloride in dioxan or tetrahydrofuran or with trifluoroacetic acid followed by treating the resulting primary amine or salt thereof (e.g. the hydrochloride salt) with acetic anhydride under basic conditions in a suitable solvent such as a halogenated hydrocarbon (eg dichloromethane).

If a salt of a compound of formula (1) is formed, the corresponding base may be obtained by addition of a suitable base.

If a compound of formula (1) is obtained as a base, a corresponding salt may be obtained by conventional means, eg by addition of an appropriate acid. The reaction may conveniently be effected in a suitable solvent at room temperature.

A salt of a compound of formula (1) may be converted into a different salt, eg a physiologically acceptable salt by addition of a suitable acid using conventional means.

The general process steps described above may yield the product of general formula (1) as an individual stereoisomer. However, when, for example, $X^3$ contains a chiral centre the product of general formula (1) may be obtained as an individual stereoisomer or as a mixture of steroisomers. Specific isomers may be separated at any convenient point in the overall synthesis by conventional methods eg chromatography.

The wiggly line notation used in formulae (10), (11), (12) and (14) means that the stereochemistry is undefined at this carbon atom.

Compounds of formulae (2), (4), (5), (10), (11) and (12) are novel, and the novel compounds form a further aspect of the present invention.

The following non-limiting Examples illustrate the invention. All temperatures are in °C.

INTERMEDIATE 1

N-[25-(Acetyloxy)-1S-cyclohexylmethyl-5-hexen-1-yl]carbamic acid, 1,1-Dimethylethyl ester A Grignard reagent was prepared from 4-bromo-1-butene (12.75 ml) and magnesium (3 g) in dry ether (60 ml). To the stirred solution, cooled in an ice-bath, was added a solution of N-[(1,1-dimethylethoxy)-carbonyl]-L-cyclohexylalaninal (12.2 g) in dry ether (20 ml) at such a rate that the reaction mixture remained at ca. 20°. The mixture was stirred at 20° for a further 15 minutes. It was then cooled in a ice-bath, and 2N-sulphuric acid (25 ml) was added dropwise to destroy the excess Grignard reagent. The mixture was partitioned between ethyl acetate (150 ml) and 2N-sulphuric acid (100 ml) and the organic layer was washed with a little water, dried ($Na_2SO_4$) and evaporated to a pale yellow oil. The oil (15.7 g) in dry dichloromethane (250 ml) was treated with pyridine (6 ml) and acetic anhydride (7.25 ml) and 4-dimethylaminopyridine (100 mg). The pale yellow solution was stirred at 20° for 20 hours, then diluted with dichloromethane (250 ml) and washed successively with 100 ml portions of water, 2N-hydrochloric acid, water, 5% sodium hydrogen carbonate solution, and water. The organic layer was dried ($Na_2SO_4$) and evaporated to an oil. The oil was purified on silica (500 g) eluted with ethyl acetate:petrol (1:19) in 250 ml fractions. Fractions 12 to 17 yielded the title compound (9.87 g) as a colourless oil, $[\alpha]_D -45°$ ($CH_2Cl_2$, c 3.4), $\delta(CDCl_3)$ 0.7 to 1.07 (m,2H), 1.07 to 1.90 (m, including 1.47, 1.49, 2s,9H), 2.09 (s and m,5H), 3.88 (m,1H), 4.47, 4.26 (2d,1H), 4.80 to 5.10 (m,3H), 5.70 to 5.90 (m,1H).

INTERMEDIATE 2

N-[25-(Acetyloxy)-1S-(cyclohexylmethyl)-4RS-ethyl-5-hexen-1-yl]carbamic acid, 1,1-dimethylethyl ester A Grignard reagent was made from 3-bromomethyl-1-pentene (4.078 g) and magnesium (550 mg) in dry ether (20 ml). The resulting cloudy solution was stirred under nitrogen and cooled in a water-bath at ca. 15°. To the stirred mixture was added a solution of N-(1,1-dimethylethoxy-carbonyl)-L-cyclohexylalaninal (1.95 g) in ether (10 ml) dropwise over 8 minutes. The mixture was stirred at 20° for 30 minutes, then cooled (ice-bath) and treated with 2N-sulphuric acid (10 ml) and water (10 ml). The mixture was diluted with ethyl acetate (150 ml) and the organic layer was washed (2N-sulphuric acid, 40 ml and water, 2×30 ml), dried (Na$_2$SO$_4$) and evaporated to a pale orange oil. This oil in dichloromethane (40 ml) was treated with pyridine (1.6 ml) and acetic anhydride (1.92 ml). 4-Dimethylaminopyridine (15 mg) was added, and the clear solution was stirred at 20° for 24 hours. The reaction mixture was diluted with dichloromethane (150 ml) and washed successively with 25 ml portions of 2N-hydrochloric acid, water, 5% sodium hydrogen carbonate solution and water. It was then dried (Na$_2$SO$_4$) and evaporated to an oil which was purified on a column of silica gel (100 g) eluted with ethyl acetate:petrol (1:4) in 50 ml fractions. Fractions 8 to 12 yield the title compound (1.17 g) as a clear oil, δ (CDCl$_3$) 0.7 to 1.05 (m,5H) 1.05 to 2.0 (m, including 1.46, s,9H), 2.03, 2.08 (2s,3H), 3.70 to 4.0 (2m,1H), 4.45 (2d,1H), 4.70 to 5.10 (m,3H), 5.40 to 5.65 (m,1H).

Intermediate 3 and 4 were prepared in a similar manner.

INTERMEDIATE 3

N-[2S-(Acetyloxy)-1S-)cyclohexylmethyl)-4RS-(1-methylethyl)-5-hexen-1-yl]carbamic acid, 1,1-dimethylethyl ester (0.65g), δ (CDCl$_3$) 0.82, 0.86 (2d,6H), 0.80 to 1.95 (m, including 1.46, s,9H), 2.03, 2.08 (2s,3H), 3,70 to 4.0 (2m,1H), 4,35 to 4.55 (2d,1H), 4,70 to 5.15 (m,3H), 5.45 to 5.65 (m,1H).

From N-(1,1-dimethylethoxycarbonyl)-L-cyclohexylalaninal (3.3 g) and 3-bromomethyl-4-methyl-b 1-pentene.

INTERMEDIATE 4

N-[25-(Acetyloxy)-1S(cyclohexylmethyl)-4RS-ethenyl-5RS-methyl-1-heptyl]carbamic acid, 1,1-Dimethylethyl ester, isolated, after chromatography as two pairs of diasteroisomers (i) the (4R, 5RS) pair of isomers (0.975 g), δ(CDCl$_3$) 0.6 to 1.0 (m,8H), 1.0 to 1.85 (m, including 1.42, s, 9H), 1.96, 2.01 (2s,3H), 2.0 to 2.15 (m,1H), 3.7 to 4.0 (2m,1H), 4.3 to 4.5 (2d,1H), 4.72 to 5.06 (m,3H), 5.4 to 5.7 (m,1H); and (ii) the (4S,5RS) pair of isomers (0.41g), δ (CDCl$_3$), 0.7 to 1.0 (m,8H), 1.0 to 2.05 (m, including 1.40,s,9H), 2.02 to 2.10 (2s,3H), 3.6 to 4.0 (m,1H), 4.3 to 4.55 (m,1H), 4.75 to 5.2 (m,3H), 5.4 to 5.7 (m,1H).

From N-(1,1-dimethylethoxycarbonyl)-L-cyclohexylalaninal (3.57 g) and 3-bromomethyl-4-methyl-1-hexene.

INTERMEDIATE 5

N-[2-Cyclohexyl-1S-(4,5-dihydro-2-oxo-3H-furan-5S-yl)ethyl]carbamic acid, 1,1-Dimethylethyl ester Intermediate 1 (9.75 g) in carbon a tetrachloride (60 ml) and acetonitrile (60 ml) and water (90 ml) was treated with ruthenium chloride trihydrate (157 mg) and sodium metaperiodate (23.8 g). The mixture was stirred vigorously for 2.5 hours, filtered, and the residue washed with water (40 ml) and dichloromethane (400 ml). The organic layer was dried (Na$_2$SO$_4$) and evaporated to give a grey foam (10 g). The foam was stirred in ethanol (160 ml) with 1N aqueous sodium hydroxide (75 ml) at 20° for 1.5 hours. The solution was acidified with 2N-hydrochloric acid (50 ml) and extracted with ethyl acetate (2×50 ml). The organic layer was washed with water (25 ml), dried (Na$_2$SO$_4$) and evaporated to an oil-water mixture, which was redissolved in ethyl acetate, dried (Na$_2$SO$_4$) and evaporated to a foam. The foam was dissolved in ethyl acetate (100 ml) and treated with N,N'-dicyclohexylcarbodiimide (5 g) in ethyl acetate (50 ml). The mixture was stirred at 20° for 40 minutes and then filtered. The filtrate was treated with acetic acid (0.1 ml), ethanol (0.1 ml) and water (0.8 ml), stirred at 20° for 45 minutes, and then evaporated to a wet solid which was left at 4° overnight. The solid was treated with ethyl acetate (150 ml) and filtered, and the filtrated was evaporated to a grey oil which was purified on silica (400 g) eluted with ethyl acetate:petrol (1:4) in 200 ml fractions. Fractions 10 to 21 yielded the title compound (5.2 g) as a pale yellow oil, $[\alpha]_D-33^4$ (CHCl$_3$, c.2); δ(CDCl$_3$), 0.72 to 1.06 (m,2H), 1.06 to 1.90 (m, including 1.42, s,9H), 1.96 to 2.32 (m,2H), 3.84 (m,1H), 4.30 to 4.54 (m,2H); $\nu_{max}$ (CHBr$_2$) 1705, 1767 (carbonyls), 3425 cm$^{-1}$ (NH).

INTERMEDIATE 6

N-[2-Cyclohexyl-1S-(3R-ethyl-4,5-dihydro-2-oxo-3H-furan-5S-yl)ethyl]carbamic acid, 1,1-dimethylethyl ester Intermediate 2 (1.05 g) in carbon tetrachloride (7ml) and acetonitrile (7 ml) was treated with ruthenium trichloride trihydrate (20 mg) and sodium metaperiodate (2.6 g) and water (10.5 ml). The brown mixture was stirred vigorously at 20° for 5 hours, partitioned between dichloromethane (200 ml) and water (50 ml), the organic layer washed with a little water, then dried (Na$_2$SO$_4$) and evaporated to a grey foam. The foam was dissolved in ethanol (25 ml) and treated with 1N-sodium hydroxide solution (10.4 ml). The solution was stirred at 20° for 2.5 hours, acidified with 1N-hydrochloric acid (20 ml) and extracted with ethyl acetate (200 ml). The organic layer was washed with a little water, then dried (Na$_2$SO$_4$) and evaporated to a wet oil which was redissolved in ethyl acetate, dried (Na$_2$SO$_4$) and evaporated to a foam. The foam was dissolved in ethyl acetate (20 ml) and treated with N,N'-dicyclohexylcarbodiimide (250 mg). The mixture was stirred at 20° for 1 hour, more dicyclohexylcarbodiimide (100 mg) was added and the mixture was stirred at 20° for a further hour. The mixture was filtered, and the filtrate was evaporated to a foam, which was redissolved in ether:ethyl acetate (1:1, 15 ml), and filtered and evaporated to a white foam. The foam was purified on a column of silica gel (100 g) eluted with ethyl acetate:petrol (1:9) in 100 ml fractions. Fractions 8 to 10 yielded the title compound (239 mg) as a soft white solid, δ(CDCl$_3$) 0.70 to 1.05 (m,2H) 1.01 (t,3H), 1.05 to 2.05 (m, including 1.47,s,9H), 2.35 (m,1H), 2.55 (m,1H), 3.88 (m,1H), 4.35 (d,1H), 4.47 (m,1H); $\nu_{max}$ (CHBr$_2$), 3410 (NH), 1760 (lactone C=O) and 1705cm$^{-1}$ (carbamate C=O).

Intermediates 7 and 8 were prepared in a similar manner.

INTERMEDIATE 7

N-[2-Cyclohexyl-1S[3S-(1-methylethyl)-4,5-dihydro-2-oxo-3H-furan-5S-yl]ethyl]carbamic acid, 1,1-dimethylethyl ester (92 mg), δ (CDCl$_3$) 0.93, 1.01 (2d,6H), 0.70 to 2.00 (m, including 1.46,s,9H), 2.00 to 2.30 (m,3H), 2.50 to 2.65 (m,1H), 3.88 (m,1H), 4,35 (d,1H), 4.43 (m,1H).

From Intermediate 3 (621 mg).

INTERMEDIATE 8

N-[2-Cyclohexyl-1S[3S-(1RS-methylpropyl)4,5-dihydro-2-oxo-3H-furan-5S-yl]ethyl]carbamic acid, 1,1-dimethylethyl ester (44 mg), δ(CDCl₃) 0.7 to 1.07 (m,8), 1.07 to 1.09 (m, including 1.45,s,9H), 1.9 to 2.35 (m,3H), 2.55 to 2.8 (2m,1H), 3,86 (m,1H), 4.36 (2d,1H), 4.4 (m,1H).

From the (4S, 5RS) pair of isomers of Intermediate 4 (480 mg).

INTERMEDIATE 9

N-[2-Cyclohexyl-1S-(3R-ethyl-4,5-dihydro-2-oxo-3H-furan-5S-yl)ethyl]-carbamic acid, 1,1-dimethylethyl ester To a 1M solution of sodium bistrimethylsilylamide (1.3 ml), diluted with tetrahydrofuran (1 ml) and cooled to −70° under nitrogen was added dropwise a solution of Intermediate 5 (155 mg) in tetrahydrofuran (0.8 ml), at a rate that maintained the reaction temperature below −65°. The resulting yellow solution was stirred at −70° for 15 minutes, then ethyl trifluoromethanesulphonate (97.9 mg) was added over 0.5 minute. After stirring at −70° for 3 hours, acetic acid (0.5 ml), then 2 N hydrochloric acid (15 ml) were added. The mixture was allowed to warm to 20°, when it was extracted with dichloromethane (2×20 ml). The combined extracts were dried (MgSO₄) and evaporated to a yellow gum. Chromatography on silica gel (10 g), eluting with ethyl acetate/hexane (1:4 v/v) yielded the title compound as a white solid (92 mg), δ(CDCl₃) 0.7–0.95 (2H, m), 0.97 (3H, t), 1.05–1.9 (13H,m), 1.45 (9H,s), 1.9–2.05 (1H,m), 2.55 (1H,m), 3.85 (1H,m), 4.35 (1H,d), 4.5 (1H,m); $\nu_{max}$ (CHBr₂) 1705, 1755, 3420 cm⁻¹.

INTERMEDIATE 10

N-[2-Cyclohexyl-1S-(3R-phenylmethyl-4,5-dihydro-2-oxo-3H-furan-5S-yl)ethyl]carbamic acid, 1,1-dimethylethyl ester

Method A

To a 0.57 M solution of lithium dissopropylamide (7 ml) in tetrahydrofuran and cooled to −70° under nitrogen was added dropwise a solution of Intermediate 5 (600 mg) in tetrahydrofuran (2 ml), at a rate that maintained the reaction temperature below −65°. The resulting yellow solution was stirred at −70° for 20 minutes, then benzyl bromide (0.69 g) was added over 1 minute. After stirring at −70° for 4.5 hours, acetic acid (0.5 ml), then 2N hydrochloric acid (25 ml) were added. The mixture was allowed to warm to 20° and then extracted with dichloromethane (3×50 ml). The combined extracts were dried (MgSO₄) and evaporated to a yellow gum. Chromatography on silica gel (30 g), eluting with ethyl acetate/hexane (1:9 v/v) then (1:4 v/v) yielded the title compound as a white solid (368 mg), δ(CDCl₃) 0.7–1.0 (2H,m), 1.0–1.8 (11H,m), 1.4 (9H,s), 1.95–2.15 (2H,m), 2.8–3.2 (2H,m), 2.95 (1H,), 3.8 (1H,m), 4.2 (1H,m), 4.3 (1H,d), 7.1–7.3 (5H,m); $\nu_{max}$ (CHBr₃) 1705, 1760, 3430 cm⁻¹.

METHOD B

To a 0.6M solution of sodium bistrimethylsilylamide (16.6 ml) in tetrahydrofuran and cooled to −70° under nitrogen added dropwise a solution of Intermediate 5 (2.5 g) in tetrahydrofuran (12 ml), at a rate that maintained the reaction temperature below −65°. The resulting yellow solution was stirred at −70° for 20 minutes, then benzyl bromide (3.42 g) was added over 3 minutes. After stirring at −70° for 4 hours acetic acid (4 ml) then 2N hydrochloric acid (25 ml) wee added. The mixture was allowed to warm to 20° and then extracted with dichloromethane (3×40 ml). The combined extracts were dried (MgSO₄) and evaporated to an oil. Chromatography on silica gel (150 g), eluting with ethyl acetate/hexane (1:9 v/v) then (1:4 v/v) yield the title compound as a white solid (348 mg). NMR analysis showed the product to be the same as that prepared according to Method A above.

INTERMEDIATE 11

N-[1S-[[3R-phenylmethyl]-2-oxo-(3H)-dihydrofuran-5S-yl]-2-cyclohexyl-ethyl]-[N-[(1,1-dimethylethoxy)-carbonyl]-L-phenylalanyl]-L-(N(im)-2,4-dinitrophenyl) histidinamide Intermediate 10 (254 mg) was stirred with a 4M solution of hydrogen chloride in dioxan (10 ml) for 20 minutes at room temperature, then evaporated to give a pale cream solid. The solid was dissolved in dimethylformamide (2 ml), then triethylamine (96 µl) and N-[(1,1-dimethylethoxy)carbonyl]-L-[N(im)-2,4-dinitrophenyl]histidine pentafluorophenyl ester (570 mg) were added, and the mixture stirred at room temperature for 1 hour. 4-(2-Aminoethyl)morpholine (130 µl) was added and the mixture stirred at room temperature for 5 minutes. The reaction mixture was diluted with ethyl acetate (50 ml) and washed with citric acid (2×30 ml), saturated sodium bicarbonate (2×30 ml), brine (30 ml), dried (MgSO₄) and evaporated to a yellow foam. The foam was stirred with a 4 M solution of hydrogen chloride in dioxan (10 ml) for 20 minutes at room temperature, then evaporated to give a yellow solid. The solid was dissolved in dimethylflormamide (2 ml), then triethylamine (96 µl) and N-[(1,1-dimethylethoxy)carbonyl -L-phenylalanine pentafluorophenyl ester (460 mg) were added and the mixture stirred at room temperature for 1 hour. 4-(2-Aminoethyl)-morpholine (130 µl) was added and the mixture stirred at room temperature for 5 minutes. The reaction mixture was diluted with ethyl acetate (50 ml), and washed with 1 citric acid (2×30 ml), saturated sodium bicarbonate (2×30 ml), brine (30 ml), dried (MgSO₄) and evaporated to a yellow solid. Chromatography on silica gel (50 g) eluting with chloroform/methanol (40:1 v/v) yielded the title compound as a yellow solid (389 mg), δ(CDCl₃) 0.7–1.0 (2H,m), 1.0–1.8 (11H,m), 1.35 (9H,s), 1.9–2.1 (2H,m), 2.8–3.2 (7H,m), 4.05 (1H,m), 4.15–4.4 (2H,m), 4.7 (1H,m), 4.95 (1H,d), 7.0 (1H,s), 7.05 (1H,d), 7.15–7.35 (10H,m), 7.6 (1H,s), 7.7 (1H,m), 7.8 (1H,d), 8.6 (1H,dd), 8.9 (1H,d).

EXAMPLE 1

N-[5-[(4-Aminobutyl)amino]-25-hydroxy-5-oxo-1S-(cyclohexylmethyl)-4R-(phenylmethyl-1-pentyl]-[N-[(1,1-dimethylethoxy)carbonyl]-L-phenylalanyl]-L-histidinamide

METHOD A

A solution of Intermediate 11 (20 mg) in 1,4-diaminobutane (0.5 ml) was kept at 40° for 20 hours, then dichloromethane (150 ml) was added. The organic phase was washed with water (30 ml), dried (MgSO₄) and evaporated to a glass, which was purified by preparative high performance liquid chromatography to give the title compound (10 mg). Mass spectrum MH+774.

METHOD B

Intermediate 10 (442 mg) was stirred with a 4M solution of hydrogen chloride in dioxan (17 ml) for 75 minutes at room temperature, then evaporated to a white solid. The solid was mixed with [N-[(1,1-dimethylethoxy)carbonyl]-L-phenylalanyl]-L-hisidine (443 mg) in dimethylformamide (3 ml) and the resulting solution cooled in an ice-bath. Diphenylphosphoryl azide (258 μl) in dimethylformamide (1 ml) and triethylamine (300 μl) in the same solvent (1 ml) were added, and the reaction stirred in an ice-bath for 2 hours, then at room temperature for 18 hours. The reaction mixture was diluted with ethyl acetate (100 ml) and washed with 10% citric acid (2×40 ml), water (30 ml), saturated sodium bicarbonate (2×30 ml), brine (30 ml), dried (MgSO$_4$) and evaporated to give a white solid. The solid was treated with 1,4-diaminobutane (2 ml) at 40° for 4 hours. The reaction mixture was added to water (50 ml) and extracted with ethyl acetate (6×50 ml), dried (MgSO$_4$) and evaporated to give a white solid, which was purified by preparative high performance liquid chromatography to yield the title compound (600 mg) as a white powder, δ(DMSO-d6) 0.7–1.0 (2H,m), 1.3 (9H,s), 1.0–1.8 (17H,m), 2.4–3.2 (11H,m) 3.3 (1H,d), 3.75 (1H,m), 4.15 (1H,m), 4.67 (1H,m), 7.05 (1H,d), 7.1–7.35 (10H,m), 7.4 (1H,s), 7.75 (4H,m), 8.3 (1H,d), 9.05 (1H,s). Mass spectrum MH$^+$ 774.

Examples 2–9 were similarly prepared according to Method B above from [N-[(1,1-dimethylethoxy)carbonyl]-L-phenylalanyl]-L-histidine, one of Intermediates 7–10 and a suitable diamine.

EXAMPLE 2

N-[5-[(4-Aminobutyl)amino]-1S-(cyclohexylmethyl)-4R-ethyl-2S-hydroxy-5-oxo-1-pentyl]-[N-[(1,1-dimethylethoxy)carbonyl]-L-phenylalanyl]-L-histidinamide (74 mg), δ (DMSO-d$_6$) 0.79 (t,3H), 0.70 to 1.83 (m, including 1.29,s,9H), 2.20 to 3.30 (m,8H), 4.13 (m,1H), 4.68 (m,1H), 7.03 (d,1H), 7.10 to 7.35 (m,5H), 7.42 (s,1H), 7.62 (d,1H), 7.92 (broad s,4H), 8.39 (d,1H), 9.04 (s,1H). Mass spectrum MH$^+$712.

From Intermediate 9 (110 mg) and 1,4-diaminobutane.

EXAMPLE 3

N-[5-[(4-Aminobutyl)amino]-1S-(cyclohexylmethyl)-2S-hydroxy-4S-(1-methylethyl)-5-oxo-1-pentyl]-[N-[(1,1-dimethylethoxy)carbonyl]-L-phenylalanyl]-L-histidinamide (28 mg), δ(DMSO-d$_6$) 0.80 (d,6H), 0.60 to 1.85 (m, including 1.28,s,9H), 2.60 to 3.30 (m,8H), 373 (m,1H), 4.13 (m,1H), 4.67 (m,1H), 7.01 (d,1H), 7.10 to 7.35 (m,5H), 7.39 (s,1H), 7.49 (d,1H), 7.72 (broad s,3H), 7.83 (m,1H), 8.33 (d,1H), 9.00 (s,1H), Mass spectrum MH+ 726

From Intermediate 7 (40 mg) and 1,4-diaminobutane.

EXAMPLE 4

N-[5-[(4-Aminobutyl)amino]-1S-(cyclohexylmethyl)-2S-hydroxy-4S-(1-RS-methylpropyl)-5 -oxo-1-pentyl]-[N-(1,1-dimethylethoxy)carbonyl)-L-phenylalanyl]-L-histidinamide (35 mg). Mass spectrum MH+ 740.

From Intermediate 8 (60 mg) and 1,4-diaminobutane.

EXAMPLE 5

N-[(1,1-Dimethethoxy)carbonyl]-L-phenylalanyl-N-[1S-(cyclohexylmethyl-2 S-hydroxy-5-[[2-(N-methylamino)ethyl]amino]-5-oxo-4R-(phenylmethyl)-pentyl]-L-histidinamide, trifluoroacetate (171 mg), δ (DMSO-d$_6$) 0.6–1.8 (15H,m), 1.30 (9H,s), 2.50–3.6 (11H,m), 3.58 (3H,s), 3.75 (1H,m), 4.13 (1H,m), 4.5–4.9 (2H,m), 6.98 (1H,d), 7.05–7.31 (10 H,m), 7.36 (1H,s), 7.45 (1H,d), 7.81 (1H,bs), 8.0 (1H,t), 8.30 (1H,d), 8.98 (1H,s). Mass spectrum MH$^+$760.

From Intermediate 10 (50 mg) and 2-(N-methylamino)ethylamine.

EXAMPLE 6

N-[(1,1-Dimethylethoxy)carbonyl]-L-phenylalanyl-N-[5-[(2-amino-2-methylpropyl) amino]-1S-(cyclohexylmethyl)-2S-hydroxy-5-oxo-4R-(phenylmethyl)pentyl]-L-histidinamide, trifluoroacetate (132 mg), δ(DMSO-d$_6$) 0.64–1.70 (15H,m), 1.30 (9H,s), 3.75 (1H,m), 4.13 (1H,m), 4.56–4.90 (2H,m), 6.99(1H,d), 7.05–7.32 (10H,m), 7.38 (1H,s), 7.50 (1H,d), 7.85 (2H,bs), 7.89 (1H,t), 8.30 (1H,d), 9.01 (1H,s). Mass spectrum MH$^+$774.

From Intermediate 10 (100 mg) and 1,2-diamino-2-methylpropane.

EXAMPLE 7

N-[(1,1-Dimethylethoxy)carbonyl]-L-phenylalanyl-N-[1S-(cyclohexylmethyl)-5-[[2-[N,N-dimethylamino)-1-methylethyl]amino]-2S-hydroxy-5-oxo-4R-(phenylmethyl)pentyl]-L-histidinamide, trifluoroacetate (30 mg), δ(DMSO-d$_6$) 0.65–1.80 (15H,m), 1.30 (9H,s), 2.48–3.12 (10H,m), 3.36 (9H,s). 7.0 (1H,d), 7.07–7.32 (10H,m), 7.35 (1H,s), 7.48 (1H,m). 7.72–7.96 (1H,m), 8.05 (1H,m), 8.30 (1H,m), 8,95 (1H,s). Mass spectrum MH$^+$788.

From Intermediate 10 (50 mg) and 1-(N,N-dimethylamino)-2-aminopropane.

EXAMPLE 8

N-[(1,1-Dimethylethoxy)carbonyl]-L-phenylalanyl-N-[1S-(cyclohexylmethyl)-2S-hydroxy-5-[[2-aminoethyl]amino]-5-oxo-4R-(phenylmethyl) pentyl]-L-histidinamide, trifluoroacetate (52 mg), δ (DMSO-d$_6$) 0.6–1.8 (15H,m), 1.30 (9H,s), 2.5–3.5 (m), 4.05–4.22 (1H,m), 4.55–4.75 (1H,m), 6.9 (1H,d), 7.1–7.3 (10H,m), 7.35 (1H,s), 7.45 (1h,d), 7.9 (1H,t), 8.25 (1H,d), 8.98 (1H,s). Mass spectrum MH$^+$746.

From Intermediate 10 (70 mg) and 1,2-diaminoethane.

EXAMPLE 9

N-[(1,1-Dimethylethoxy)carbonyl]-L-phenylalanyl-N-[1S-(cyclohexylmethyl)-2S-hydroxy-5S-hydroxy-5-[[2-(N,N-dimethylamino)ethyl]amino]-5-oxo-4R-(phenylmethyl)pentyl]-L-histidinamide, trifluoroacetate (79 mg), δ(DMSO-d$_6$) 0.6–1.8 (15H,m), 1.29 (9H,s), 2.50–3.66 (12H,m), 2.70 (6H,s), 3.65–3.80 (1H,m), 4.05–4.20 (1H,m), 4.67–4.7 (1H,m), 7.0 (1H,d), 7.1–7.3 (10H,m), 7.38 (1H,s), 7.5 (1H,d), 8.05 (1H,t), 8.32 (1H,d), 9.0 (1H,s). Mass spectrum MH$^+$774.

From Intermediate 10 (70 mg) and 2-(N,N-dimethylamino)ethylamine.

EXAMPLE 10

N-[5-[(4-Aminobutyl)amino]-2S-hydroxy-5-oxo-1S-(cyclohexylmethyl)-4R-(phenylmethyl)-1-pentyl]-[N-acetyl-L-phenylalanyl]-L-histidinamide

METHOD A

The product of Example 1 (40 mg) was stirred with a 4M solution of hydrogen chloride in dioxan (1 ml) for 45 minutes at room temperature, then evaporated to an opaque glass. This was dissolved in dichloromethane (1 ml), then acetic anhydride (39 μl) and triethylamine (114 μl) were added and the reaction stirred at room temperature for 2 hours. The reaction mixture was diluted with dichloromethane (50 ml) and washed with 1N citric acid (2×30 ml), saturated sodium bicarbonate (2×30 ml), brine (30 ml) dried (MgSO4) and evaporated to an orange solid. The solid was treated with 1,4-diaminobutane (0.5 ml) at 40° for 16 hours and at 20° for 24 hours. The reaction mixture was diluted with dichloromethane (150 ml) and washed with water (30 ml), dried (MgSO4) and evaporated to give a red solid, which was purified by preparative high performance liquid chromatography to yield the title compound (8 mg). Mass spectrum MH+716.

METHOD B

Intermediate 10 (49.8 mg) was stirred with a 4M solution of hydrogen chloride in dioxan (2 ml) for 45 minutes at room temperature, then evaporated to give a pale cream solid. The solid was mixed with N-[acetyl-L-phenylalanyl]-L-histidine (42.7 mg) in dimethylformamide (1 ml) and the resulting solution cooled in an ice-bath. Diphenylphosphoryl azide (34 μl) and triethylamine (38 μl) were added and the reaction stirred in an ice-bath for 2 hours, then at room temperature for 16 hours. The reaction mixture was diluted with ethyl acetate (50 ml), washed with 2N hydrochloric acid (2×30ml), saturated sodium bicarbonate (2×30 ml), saturated brine (30 ml), dried (MgSO4) and evaporated to a sticky gum. Chromatography on silica gel (2g) eluting with chloroform/methanol (19:1 v/v) afforded a white foam. The foam was treated with 1,4-diaminobutane (1 ml) and heated at 60° for 1.5 hours. The reaction mixture was diluted with chloroform (150 ml), washed with water (30 ml), dried (MgSO4) and evaporated to give a white foam, which was purified by preparative high performance liquid chromatography to yield the title compound (30 mg). Mass spectrum MH+716.

We claim:

1. Compounds of formula (I)

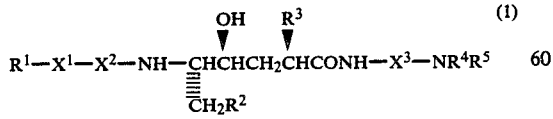

wherein:
R$^1$ represents an acyl group;
X$^1$ is selected from phenylalanine and p-methoxyphenylalanine bonded N-terminally to R$^1$ and C-terminally to X$^2$;
X$^2$ is selected from histidine and N-methylhistidine bonded N-terminally to X$^1$ and C-terminally to the group —NH—;
R$^2$ represents a C$_{4-6}$ cycloalkyl group;
R$^3$ represents a group CHR$^6$R$^7$ (where R$^6$ is a hydrogen and R$^7$ is phenyl, or R$^6$ is methyl and R$^7$ is selected from hydrogen, methyl and ethyl;
X$^3$ represents a C$_{2-6}$ alkylene chain optionally substituted by one or more C$_{1-4}$ alkyl groups;
R$^4$ and R$^5$, which may be the same or different, each independently is selected from hydrogen and C$_{1-4}$ alkyl group, or NR$^4$R$^5$ forms a 5- or 6-membered polymethylenimine ring;
and physiologically acceptable salts and solvates thereof.

2. Compounds of formula (I) as claimed in claim 1 wherein R$^1$ represents a group R$^8$X$^4$C(=O)—, wherein R$^8$ is a C$_{1-6}$ alkyl group and X$^4$ is an oxygen atom or a bond;
R$^2$ is selected from cyclopentyl and cyclohexyl;
R$^3$ represents a group —CHR$^6$R$^7$ wherein R$^6$ represents hydrogen and R$^7$ represents phenyl, or R$^6$ is methyl and R$^7$ is selected from hydrogen, methyl and ethyl;
X$^3$ represents a C$_{2-4}$ alkylene chain optionally substituted by one or two methyl groups; and
R$^4$ and R$^5$ each independently represents hydrogen atom or methyl;
and physiologically acceptable salts and solvates thereof.

3. Compounds of formula (Ia)

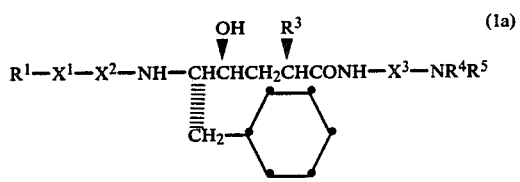

wherein R$^1$ represents a group R$^8$x$^4$C(=O)—, where R$^8$ is a C$_{1-4}$ alkyl group and X$^4$ is an oxygen atom or a bond; X$^1$, X$^2$ and R$^3$ are as defined in formula (1) in claim 1; X$^3$ represents a C$_{2-4}$ alkylene chain optionally substituted by one or two methyl groups; and R$^4$ and R$^5$ are each independently selected from hydrogen and methyl; and physiologically acceptable salts and solvates thereof.

4. Compounds as claimed in claim 3 wherein R$^1$ is selected from acetyl and t-butoxycarbonyl,
X$^1$ represents phenylalanine,
X$^2$ represents histidine,
R$^3$ represents a group —CHR$^6$R$^7$ wherein R$^6$ represents a hydrogen atom and R$^7$ represents methyl or phenyl, X$^3$ represents a C$_{2-4}$ alkylene chain selected from —(CH$_2$)$_2$—, —CH$_2$CH(CH$_3$)—, and —(CH$_2$)$_4$— and R$^4$ and R$^5$ each independently represent hydrogen or methyl; and physiologically acceptable salts and solvates thereof.

5. A compound of formula (I) as claimed in claim 1 which is N-[(1,1-dimethylethoxy)carbonyl]-L-phenylalanyl-N-[1S-(cyclohexylmethyl)-2S-hydroxy-5-[[2-aminoethyl]amino]-5-oxo-4R-(phenylmethyl) pentyl]-L-histidinamide, and physiologically acceptable salts and solvates thereof.

6. The physiologically acceptable salts and solvates of compounds of formula (I) as claimed in claim 1.

7. A method of combatting disorders in a human or veterinary subject selected from hypertension, hyperaldosteronism, cardiac insufficiency, congestive heart failure, post-myocardial infarction; cerebrovascular disorders, glaucoma or disorders of intracellular homeostasis, which comprises administering to said subject an effective amount of a compound of formula (I) as claimed in claim 1.

8. A pharmaceutical composition comprising a compound of formula (1) as claimed in claim 1, or a physiologically acceptable salt or solvate thereof, in combination with a pharmaceutically acceptable carrier, diluent or excipient.

9. A process for preparing the compounds of formula (1) as defined in claim 1 which comprises reacting a lactone of formula (2)

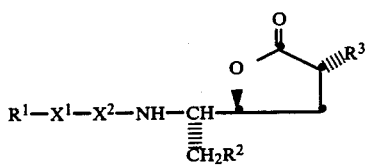

(2)

wherein $R^1$, $R^2$, $R^3$, $X^1$ and $X^2$ are as defined in claim 1, with a diamine of formula (3)

$$R^5R^4N-X^3-NH_2$$ (3)

wherein $R^4$, $R^5$ and $X^3$ are as defined in claim 1, or a protected derivative thereof, followed if necessary or if desired, by removal of any protecting groups present and, if desired, by salt formation.

10. The physiologically acceptable salts and solvates of compounds of formula (1a) as claimed in claim 3.

11. A process according to claim 9, wherein the process is carried out in the absence or presence of a suitable solvent at a temperature in the range of room temperature to 80° C.

12. A process according to claim 11 wherein an alcohol or a halogenated hydrocarbon is present as the solvent.

13. A method according to claim 7 wherein the disorder is hypertension.

14. A pharmaceutical composition according to claim 8 wherein the compound of formula (1) is administered to an adult human in unit dosage form in a range of 5 mg to 3 g.

15. A pharmaceutical composition according to claim 14 wherein the range is 25 mg to 1 g.

16. Compounds of formula (1) as defined in claim 1 wherein the salts are selected from the group consisting of hydrochlorides, hydrobromides, sulphates, phosphates, nitrates, benzoates, naphthoates, hydroxynapthoates, p-toluenesulphonates, methanesulphonates, sulphamates, ascorbates, oxalates, tartrates, salicylates, succinates, lactates, glutarates, glutaconates, acetates, trifluoroacetates, tricarballylates, citrates, fumarates and maleates, and wherein the solvates are hydrates.

17. Compounds as claimed in claim 2 wherein the salts are selected from the group consisting of hydrochlorides, hydrobromides, sulphates, phosphates, nitrates, benzoates, naphthoates, hydroxynaphthoates, p-toluenesulphonates, methanesulphonates, sulphamates, ascorbates, oxalates, tartrates, salicylates, succinates, lactates, glutarates, glutaconates, acetates, trifluoroacetates, tricarballylates, citrates, fumarates and maleates, and wherein the solvates are hydrates.

18. Compounds as claimed in claim 3 wherein the salts are selected from the group consisting of hydrochlorides, hydrobromides, sulphates, phosphates, nitrates, benzoates, naphthoates, hydroxynaphthoates, p-toluenesulphonates, methanesulphonates, sulphamates, ascorbates, oxalates, tartrates, salicylates, succinates, lactates, glutarates, glutaconates, acetates, trifluoroacetates, tricarballylates, citrates, fumarates and maleates, and wherein the solvates are hydrates.

19. Compounds as claimed in claim 4 wherein the slats are selected from the group consisting of hydrochlorides, hydrobromides, sulphates, phosphates, nitrates, benzoates, naphthoates, hydroxynaphthoates, p-toluenesulphonates, methanesulphonates, sulphamates, ascorbates, oxalates, tartrates, salicylates, succinates, lactates, glutarates, glutaconates, acetates, trifluoroacetates, tricarballylates, citrates, fumarates and maleates, and wherein the solvates are hydrates.

20. Compounds as claimed in claim 5 wherein the slats are selected from the group consisting of hydrochlorides, hydrobromides, sulphates, phosphates, nitrates, benzoates, naphthoates, hydroxynapthoates, p-toluenesulphonates, methanesulphonates, sulphamates, ascorbates, oxalates, tartrates, salicylates, succinates, lactates, glutarates, glutaconates, acetates, trifluoroacetates, tricarballylates, citrates, fumarates and maleates, and wherein the solvates are hydrates.

* * * * *